(12) United States Patent
Kolen et al.

(10) Patent No.: US 8,909,334 B2
(45) Date of Patent: Dec. 9, 2014

(54) ELECTRICAL STIMULATION DEVICE FOR LOCATING AN ELECTRICAL STIMULATION POINT AND METHOD

(75) Inventors: Alexander Franciscus Kolen, Eindhoven (NL); Femke Wagemakers, Eindhoven (NL); Maarten Peter Bodlaender, Eindhoven (NL); Ron Kroon, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 706 days.

(21) Appl. No.: 13/132,691

(22) PCT Filed: Dec. 3, 2009

(86) PCT No.: PCT/IB2009/055473
§ 371 (c)(1),
(2), (4) Date: Jun. 3, 2011

(87) PCT Pub. No.: WO2010/064206
PCT Pub. Date: Jun. 10, 2010

(65) Prior Publication Data
US 2011/0264002 A1    Oct. 27, 2011

(30) Foreign Application Priority Data

Dec. 5, 2008   (EP) ..................................... 08170763

(51) Int. Cl.
*A61B 5/00*      (2006.01)
(52) U.S. Cl.
USPC .......................................................... 600/547
(58) Field of Classification Search
CPC ............. A61B 5/05; A61B 5/053; A61B 5/11
USPC ......... 600/548, 546, 554, 373, 372, 382, 547, 600/377; 607/48
See application file for complete search history.

(56) References Cited

U.S. PATENT DOCUMENTS 3,817,254 A * 6/1974 Maurer ........................... 607/46
4,148,321 A * 4/1979 Wyss et al. ..................... 607/67
4,177,819 A * 12/1979 Kofsky et al. .................. 607/63

(Continued)

FOREIGN PATENT DOCUMENTS

WO        WO9952588 A1    10/1999

OTHER PUBLICATIONS

Farina D et al: "Stimulation artifact in surface EMG signal: effect of the stimulation waveform, detection system, and current amplitude using hybrid stimulation technique" IEEE Transactions on Neural Systems and Rehabilitationengineering, IEEE Service Center, New York, NY, US, vol. 11, No. 4, 1 Dec. 2003, pp. 407-415, XP011106038.

*Primary Examiner* — Max Hindenburg
(74) *Attorney, Agent, or Firm* — Larry Liberchuk

(57) ABSTRACT

An electrical stimulation device and method of locating an electrical stimulation point of a human or animal. The device comprises a matrix of electrodes distributed on an electrode pad configured to be applied on a human or animal body and arranged for covering a plurality of the stimulation points of the human or animal. An electronic circuit is connected to the matrix of electrodes and configured for applying an electrical stimulation signal to the electrodes. A feedback signal, in response to an electrical stimulation signal, may be used in assessing the suitability of electrodes as an electrical stimulation point.

20 Claims, 5 Drawing Sheets

(56) References Cited

U.S. PATENT DOCUMENTS

| | | | |
|---|---|---|---|
| 4,492,233 A * | 1/1985 | Petrofsky et al. | 607/48 |
| 4,528,984 A * | 7/1985 | Morawetz et al. | 607/59 |
| 4,934,368 A * | 6/1990 | Lynch | 607/2 |
| 4,976,264 A * | 12/1990 | Petrofsky | 607/48 |
| 5,038,781 A * | 8/1991 | Lynch | 607/61 |
| 5,425,752 A * | 6/1995 | Vu'Nguyen | 607/72 |
| 5,640,212 A * | 6/1997 | Baccarini | 348/671 |
| 5,775,331 A | 7/1998 | Raymond | |
| 5,824,027 A * | 10/1998 | Hoffer et al. | 607/118 |
| 7,221,980 B2 * | 5/2007 | Kotlik et al. | 607/48 |
| 7,280,871 B2 * | 10/2007 | Davis et al. | 607/48 |
| 7,804,545 B2 * | 9/2010 | Burnworth et al. | 348/705 |
| 8,072,338 B2 * | 12/2011 | Rondoni et al. | 340/573.5 |
| 8,265,763 B2 * | 9/2012 | Fahey | 607/48 |
| 8,532,735 B2 * | 9/2013 | Gleich | 600/407 |
| 8,585,620 B2 * | 11/2013 | McBean et al. | 601/5 |
| 2003/0074039 A1 * | 4/2003 | Puskas | 607/118 |
| 2003/0130706 A1 | 7/2003 | Sheffield | |
| 2005/0251221 A1 * | 11/2005 | Zdravkovic | 607/46 |
| 2005/0277844 A1 * | 12/2005 | Strother et al. | 600/546 |
| 2006/0015470 A1 * | 1/2006 | Lauer et al. | 706/8 |
| 2006/0206162 A1 | 9/2006 | Wahlstrand | |
| 2007/0106342 A1 * | 5/2007 | Schumann | 607/46 |
| 2008/0119918 A1 * | 5/2008 | Zdravkovic | 607/116 |
| 2009/0209878 A1 * | 8/2009 | Sanger | 600/546 |
| 2010/0298916 A1 * | 11/2010 | Rabischong et al. | 607/116 |
| 2011/0264002 A1 * | 10/2011 | Kolen et al. | 600/554 |

* cited by examiner

ELECTRICAL STIMULATION DEVICE FOR LOCATING AN ELECTRICAL STIMULATION POINT AND METHOD

FIELD OF THE INVENTION

The invention relates to an electrical stimulation device for locating an electrical stimulation point to electrically stimulate a muscle and/or a nerve of a human or animal.

The invention also relates to a method of locating an electrical stimulation point.

BACKGROUND OF THE INVENTION

Such an electrical stimulation device is for instance used in the fields of functional electro-stimulation (also often indicated as FES) and in the fields of pain suppression via electrical stimulation signal (also often indicated as transcutane electronic nerve stimulation, or in short TENS). In both FES and TENS electrical signals are locally applied to the body of a human or animal so as to excite particular parts of the nervous system. In particular a small electrical current is locally applied to the skin of the human or animal undergoing electro-stimulation. It has been found that such electro-stimulation has various beneficiary effects. As indicated above, pain suppression is one of the beneficial effects known. Furthermore, it has also been found that local electro-stimulation can activate muscular tissue and may activate the healing of wounds. In order to achieve optimum beneficiary effects, the electrical signals are to be applied to particular, optimum positions on the person or animal skin. It is known that some optimum positions on the skin have locally different electrical impedance values, hence optimum stimulation positions may be derived from electrical impedance measurements.

Such an electro-stimulation apparatus is known from the patent application WO 99/52588. The known electro-stimulation apparatus as disclosed in the cited patent application comprises an electrode system which measures local electrical impedance. The electrode system includes a multitude of electrode pads and a counter electrode held at a reference voltage.

A drawback of the known electro-stimulation apparatus is that the correct placement of the electrode for applying electrical stimulation for pain suppression still requires considerable anatomical and physiological knowledge and experience.

SUMMARY OF THE INVENTION

It is an object of the invention to provide an electrical stimulation device in which only very little anatomical knowledge and experience is required for the placement of the electrode.

According to a first aspect of the invention the object is achieved with an electrical stimulation device for locating an electrical stimulation point of a human or animal, the electrical stimulation device comprising:

a matrix of electrodes distributed on an electrode pad being configured to be applied on the human or animal body, the distribution of the electrodes in the matrix being arranged for covering a plurality of stimulation points of the human or animal, an electronic circuit being connected to the electrodes of the matrix, and being configured for applying an electrical stimulation signal to the electrodes of the matrix, and feedback means for providing a feedback signal to the electrical stimulation device in response to the applied electrical stimulation signal, the electrical stimulation device being configured for sequentially applying the electrical stimulation signal to subsets of electrodes of the matrix, and for receiving the feedback signal in response to the applying of the electrical stimulation signal to the subsets of electrodes.

The subset of electrodes may be a single electrode of the matrix, and as such the sequential applying of the electrical stimulation signal may result in sequentially applying the electrical stimulation signal to all electrodes of the matrix. Alternatively, the electrical stimulation signal may be applied to more than one electrode simultaneously, forming the subset of electrodes.

The electrical stimulation signal causes a feedback signal which is used in assessing the suitability of the subset of electrodes as an electrical stimulation point of the human or animal. By sequentially applying the electrical stimulation signal to the subsets of electrodes and by evaluating the feedback signal, the suitability of the electrodes of the matrix of electrodes as electrical stimulation point is tested by the electrical stimulation device. As such, the initial location of the matrix of electrodes may be located at a location where an optimum electrical stimulation point may be located, for example, based on a rough estimate of a lay man's knowledge of the human or animal anatomy. Due to the sequential applying of the electrical stimulation signal to sets of electrodes, the electrodes of the matrix located near to the electrical stimulation point will typically provide a predefined feedback which is recognised and which will enable the electrical stimulation device to locate the best electrode or the best subset of electrodes as electrical stimulation point.

The feedback signal may be a signal generated by the human or animal body in response to the applied electrical stimulation signal. Such feedback signal may be measurable at, for example, the skin of the human or animal. Due to the electrical stimulation signal, for example, muscle tissue may move or get activated which may be sensed at the skin of the human or animal body via known vibration measurements or via known electrical measurements such as, for example, electromyogram signals. Alternatively, the electrical stimulation signal may generate a visible muscle movement which may be clearly identified, even by a lay man. Due to the applying of the electrical stimulation signal, for example, a specific finger on the hand may move or twitch, or a specific muscle on the lower arm may move or twitch which may be visible and which may be clearly identified. In such a situation, the feedback signal may be generated by an operator of the electrical stimulation device to indicate whether the specific muscle-movement has been visually identified and as such is confirmed to the electrical stimulation device by, for example, triggering a switch generating the feedback signal.

Due to the use of the matrix of electrodes and due to the sequential applying of the electrical stimulation signal and the registration of the feedback in response to the applied electrical stimulation signal to the subset of the electrodes, the exact location of the matrix of electrodes is less critical. The electrical stimulation device tests the suitability of the individual electrodes or the individual subsets of electrodes to see which electrode is near to the stimulation point and as such identifies the electrode or subset of electrode suitable for use as stimulation electrode for applying the stimulation signal. Subsequently, when the electrical stimulation device has identified a suitable electrode or subset of electrodes, the electrical stimulation device may switch to a required stimulation signal to be applied via the selected electrode or subset of electrodes. The required stimulation signal may, for example, be a FES signal for muscle stimulation, or, for example, a TENS signal for pain suppression, or, for example, a TENS/FES combination signal to both provide muscle stimulation and pain suppression simultaneously.

In the known electro-stimulation apparatus according to WO99/52588 the known electro-stimulation apparatus comprises an electrode system which measures local electrical impedance. Although the impedance of the electrode provides an indication that a nerve may be nearby, it may still provide the wrong feedback to the human or to a therapist applying the matrix of electrodes. Furthermore, specific electrical stimulation points may be located deeper into the body of the human or animal, for example, partially motor-points covered by other muscle fibers, and thus may not be identified as suitable electrical stimulation points by simple impedance measurement. In the electrical stimulation device according to the invention the electrical stimulation device causes a feedback signal in response to the applying of the electrical stimulation signal sequentially via an electrode or via a subset of electrodes. This feedback signal is registered and provides information regarding the suitability of the specific electrode to apply the required electrical stimulation. Selecting the electrical stimulation signal to be a nerve stimulation signal for generating muscle activity enables the active response to be clearly identified as, for example, a muscle movement or a muscle twitch. Applying this electrical stimulation signal to the electrodes or to subsets of electrodes of the matrix of electrodes, the location of electrical stimulation points within the matrix of electrodes can be identified. Looking at the type of response, for example, which muscle or muscles twitches or moves or a level of muscle contraction, the electrical stimulation point may be accurately identified. Alternatively, for example, the activation of the muscle or muscles may be measured using electrical measurement techniques. As such, even when the matrix of electrodes is not accurately positioned on the human or animal body, the electrical stimulation device identifies the electrode of subset of electrodes which are nearest to the optimal stimulation point which may subsequently be used to apply the required stimulation signal.

A further benefit of the electronic stimulation device according to the invention is that it makes the search for the right location to apply, for example, pain suppression signal more pleasant for the human or animal. Signals used for pain suppression typically have a relatively high intensity compared to signals used for evoking muscle contraction via, for example, Aα-nerves. When the pain suppression signal is applied at the wrong location they may induce Aδ-nerve and/or C-nerve stimulation resulting in pain sensations to the human or animal rather than reduce the pain. By using the electronic stimulation device according to the invention, an initial identification of the correct stimulation points is done by sequentially applying the electrical stimulation signal. This electrical stimulation signal for identifying the correct stimulation points, for example, has reduced signal intensity compared to the pain suppression signal. When the right location is found, the electrical stimulation device according to the invention may switch to the more intense pain suppression signal. The pain suppression signal may differ in more ways from the initial electrical stimulation signal than only have different intensity.

In an embodiment of the electrical stimulation device, a feedback of the human or animal to the electrical stimulation signal comprises visible muscle movement, and wherein the feedback means comprise a switch for generating the feedback signal via the human or animal or a therapist activating the switch. As indicated above, an active response may occur when the electrode is applied in the vicinity of a nerve or nerve bundle via muscle contraction when the electrical stimulation signal is applied. Subsequently, the human or animal or the therapist may recognise the right muscle twitch or muscle movement and may respond to the applied electrical stimulation signal by activating the switch to generate the feedback signal. So the activation of the button or switch for generating the feedback signal may be done by the human or animal. Alternatively, an operator or therapist may be present for operating the electrical stimulation device and, for example, assisting in correctly applying the matrix of electrodes. This operator or therapist may also activate the button or switch for generating the feedback signal. The operator may, for example, be a doctor, a nurse or a technician applying the electrode to the human or animal.

So, an effect of the electrical stimulation device according to the invention is that visible muscle movement of the human or animal when applying the electrical stimulation signal is used to determine whether the location of the current electrode or subset of electrodes from the matrix of electrodes is a correct location before applying any further electrical stimulation signal, for example, a pain suppression signal. Due to the visible muscle movement in response to the electrical stimulation signal, only very little anatomical and physiological knowledge and/or experience is required for correctly placing the matrix of electrodes of the electrical stimulation device. As long as the matrix of electrodes is large enough that it covers several stimulation points, a right stimulation point may be found. As the visible muscle movement clearly indicates whether the location of the current electrode is near the required stimulation point, activation of the signal for pain suppression only commences when the right location is obtained. In case none of the electrodes of the matrix of electrodes generate the predefined visible muscle movement, the matrix of electrode may, for example, be relocated to see whether a next location would provide the predefined visible muscle movement.

Different electrical signals may be applied to the human or animal which each have a specific predefined effect. For example, an electrical signal for nerve stimulation for generating muscle activity may have a specific pulse-duration and frequency which may be different from an electrical signal for pain suppression. Furthermore, the location of the nerves which are targeted by the electrical signal may require the intensity of the electrical signal to be different. For example, when targeting Aα nerves for generating muscle activity in humans or animals the intensity is relatively low. When targeting Aβ nerves which are used to suppress pain, the intensity of the electrical signal typically is higher. Further increasing the intensity of the electrical signal, Aδ nerves may be targeted which are used for fast pain signals. Such signals may be very unpleasant to the human or animal. The electrical signals for targeting C-nerves is even further increased. As the C-nerves are used in the human or animal body for relatively slow pain signals, also these electrical signals may be very unpleasant to the human or animal. Finally, by further increasing the intensity of the electrical signal, muscle tissue may be directly stimulated. For stimulating a muscle, either an Aα nerve may be targeted in a bundle of nerves or a motor-point may be targeted. The motor-point is an interface point between the Aα nerve and the muscle. As such, choosing the electrical stimulation signal to be the nerve stimulation signal for generating muscle activity enables visible muscle contraction to be identified when the electrode or subset of electrodes from the matrix which is near the nerve or nerve bundle is activated. Such nerve stimulation signal for generating muscle activity would substantially not generate the required muscle activity when applied away from the nerve or nerve bundle, for example, directly on the muscle. As such, when a predefined muscle activity is registered, a feedback signal may be provided to the electrical stimulation device by activating the switch. This predefined muscle activity, for example, only occurs when the current electrode or subset of electrodes from the matrix is located near the targeted nerve bundle which may also be used for pain suppression. Subsequently, the predefined muscle activity indicates that the correct location is found and the pain suppression signal may commence for effectively suppressing the pain of the human or animal. In case the predefined muscle contraction is not registered, the matrix of electrodes may be relocated after which the sequential applying of the electrical stimulation signal may start again to find the predefined location.

In an embodiment of the electrical stimulation device, the feedback means comprise sensing means for sensing a feedback of the human or animal in response to the applied electrical stimulation signal. The sensing means may, for example, be a sensor for sensing an electromyogram signal, and/or for sensing an electroencephalogram signal, and/or for sensing a magnetoencaphalogram signal in response of the electrical stimulation signal. Alternatively, the sensing means may be an acoustic sensor or a piezo-electric sensor for sensing muscle movement.

In an embodiment of the electrical stimulation device, at least a further subset of electrodes is configured for electrically sensing the feedback of the human or animal in response to the applied electrical stimulation signal, the feedback signal being the sensed electrical response sensed by the further subset of electrodes. A benefit of this embodiment is that due to the fact that the electrical stimulation device comprises a matrix of electrodes and that only a subset of the electrodes is simultaneously used for applying the electrical stimulation signal, the remaining electrodes of the matrix of electrodes may be available for sensing the feedback signal, for example, via sensing an electromyogram signal. As such, the use of the further subset for electrically sensing the feedback would improve the quality of the feedback as no subjective visible muscle movement is used for generating the feedback signal. However, for using the further subset of electrodes for sensing the feedback generally requires additional electronics to be presents in the electronic circuit enabling an accurate measurement of a relatively weak electromyogram signal after having applied a relatively strong electrical stimulation signal.

In an embodiment of the electrical stimulation device, the electrodes of the matrix are both used for applying the electrical stimulation signal and configured for electrically sensing the feedback of the human or animal in response to the applied electrical stimulation signal. The feedback signal may, for example, comprise the sensed electrical response sensed by the electrodes. A benefit of this embodiment is that the electrical stimulation device is able to sense at the exact same location as the electrical stimulation signal is applied. Especially when identifying possible stimulation points, it may be beneficial to see whether the signal strength of the feedback signal measured at or near the exact same location as where the electrical stimulation signal is applied is relatively strong. For example, when applying an electrical stimulation signal to a nerve bundle located at a distance from the muscle, the strongest feedback signal is substantially not measured at or near the same location as where the electrical stimulation signal is applied, as the nerve bundle does not generate the electromygram feedback. Alternatively, when applying the electrical stimulation signal directly to a motor point, thus near or at the muscle to be stimulated, the electrode which provides the electrical stimulation signal will also measure a relatively strong electromygram feedback signal. As such, the current embodiment enables to more specifically identify stimulation points as motor points or as nerve stimulation points.

In an embodiment of the electrical stimulation device, the electrical stimulation device is configured for clipping the sensed electrical response sensed by the electrodes via: disabling measurement during predefined time-window after applying stimulation signal. For example, a time-window of 2 milliseconds directly after the stimulation pulse may be sufficient to clip the sensor after the electrical stimulation signal is applied. A shorter time-window may be possible, depending, for example, on the sensing circuit in the electronic simulation device. Alternatively, the sensed electrical response may be clipped using diode-based clipping circuitry.

In an embodiment of the electrical stimulation device, the electrical stimulation device is configured for applying the electrical stimulation signal to subsets of electrodes and for subsequently sensing the feedback using a plurality of electrodes from the matrix distributed across the matrix for sensing the feedback. A benefit when using a plurality of electrodes distributed across the matrix of electrodes is that it allows to obtain a so called feedback-map showing a distribution of possible measurement points across an area resulting from the electrical stimulation signal. Such feedback-map may be used to, for example, to identify a specific location on the human or animal body where the matrix of electrodes is currently applied. Using such feedback-map may enable the electrical stimulation device to find already identified electrical stimulation points relatively easily.

In an embodiment of the electrical stimulation device, the electrical stimulation device is configured for comparing the feedback sensed using a plurality of electrodes distributed across the matrix with a stored feedback. This stored feedback may be, for example, a feedback-map of earlier measurements of the electrical stimulation device. Alternatively, the stored feedback may be generated by the producer of the electrical stimulation device and may represent specific locations on the human or animal body which are relatively common for applying electrical stimulation signals. Using such feedback-map may identify the required stimulation location after a single applying of the electrical stimulation signal at a certain location within the matrix of electrodes. The comparison with a stored feedback enables to identify what body-part the matrix is applied to and how far the matrix is shifted and/or rotated in a certain direction with respect to the stored feedback. If the stored feedback also comprises the preferred stimulation location, the electrical stimulation device may, from the information of the shift and/or rotation of the matrix with respect to the stored feedback, directly derive which electrode or subset of electrodes to use for providing the electrical stimulation signal. Furthermore, the stored feedback may comprise different stimulation points, for example, a preferred FES stimulation point and a preferred TENS stimulation point to suppress pain when stimulating the muscle via the FES point. In such a way, a misalignment of the matrix of electrodes is quickly identified and may quickly be electrically compensated for by choosing an electrode or subset of electrodes based on the sensed misalignment information.

In an embodiment of the electrical stimulation device, the electrical stimulation device is configured for identifying a motor point as electrical stimulation point when feedback signals of substantial equal strength are measured at electrodes located around the electrode used for applying the electrical signal. As indicated before, the identification of a motor point or a nerve stimulation point may be beneficial. For example, a motor point may be used to activate a specific muscle in the human or animal body. This stimulation of the muscle may be painful to the human or animal when the human or animal is recovering from, for example, a stroke. In such case, also pain suppression may be applied near the muscle to still stimulate the muscle without it being painful to the human or animal. However, the TENS stimulation signal may preferably be applied to a nerve bundle rather than to a muscle. In the current embodiment of the electrical stimulation device, the electrical stimulation device can identify a motor-stimulation point and as such discriminate between motor-point stimulation points and nerve-bundle stimulation points, thus ensuring that the right electrical stimulation signal is applied at the right location.

The electrical stimulation device according to the invention may, for example, be configured for applying a stimulation signal comprising a pain suppression signal as the electrical stimulation signal via the electrode in response to a predefined feedback signal. If, for example, the feedback indicates that the electrode or subset of electrodes is near a nerve bundle, the electrical stimulation device may initiate pain suppression.

In an embodiment of the electrical stimulation device, the electrical stimulation device is configured for sequentially reapplying a further electrical stimulation signal to subsets of electrodes of the matrix, the further electrical stimulation signal having different intensity compared to the electrical stimulation signal. The further electrical stimulation signal may, for example, have increased signal intensity. In such an embodiment, the electrical stimulation points which are located deeper into the body or which may at least partially be covered by a further muscle, may be activated by the electrical stimulation signal and as such, also these electrical stimulation points may be found by the electrical stimulation device according to the invention. In such a second scan of the electrodes of the matrix of electrodes, the electrical stimulation device may be configured for skipping already found stimulation points because these already found stimulation points may react relatively strong to the further electrical stimulation signal which is unnecessary (as they have already been identified) and which may be painful to the human or animal.

Alternatively, the further electrical stimulation signal may have reduced signal intensity. This second scanning of the electrodes of the matrix using the electrical stimulation signal having reduced intensity may identify the stimulation points of the previously found stimulation points which are located near the surface of the skin and thus require less intense stimulation signals.

In an embodiment of the electrical stimulation device, the electrical stimulation device is configured for measuring an impedance of the electrodes before applying the electrical stimulation signal and/or before applying the further electrical stimulation signal. An initial measurement of the impedance of the electrodes enables to check whether it makes sense to apply the electrical stimulation signal at specific electrode locations. If the impedance measured at the electrode location is not below a certain threshold, applying of the test-signal would probably not result in any feedback at all. Still, care should be taken as the impedance measurement typically only identifies electrical stimulation points which are located near the surface of the skin. Also other stimulation point may be required and must be found and thus impedance measurement only would typically not be sufficient.

Furthermore, the initial impedance measurement may be used to adjust the signal parameters of the electronic stimulation signal, for example, may be used to adjust the strength of the applied electronic stimulation signal such that if the electrode is near the right location, the predefined feedback signal may be expected. For example, when the electronic stimulation signal is the nerve stimulation signal for generating muscle activity, the test-signal may only generate a muscle activation when the signal strength exceeds a specific limit. This specific limit may depend on the impedance value of the electrode location.

Even further, this embodiment may be used as a check whether the matrix of electrodes is adequately attached to the body. When the matrix of electrodes is not adequately attached to the body, applying the electrical stimulation signal at not adequately attached locations may be relatively painful to the human or animal, which may be prevented by initial impedance measurements.

Finally, by measuring the impedance of a plurality of electrodes, for example, distributed across the matrix of electrodes, again some kind of an impedance-map may be measured, comparable to the feedback-map mentioned earlier. Also such impedance-map may be used to, for example, to identify a specific location on the human or animal body where the matrix of electrodes is currently applied. Furthermore, such impedance-map may enable the electrical stimulation device to find already identified electrical stimulation points relatively easily. The impedance-map measured may also be compared to stored maps which indicate preferred TENS or FES locations.

In an embodiment of the electrical stimulation device, the electrical stimulation signal comprises a test-signal and/or a pain suppression signal and/or an electrical stimulation signal for generating muscle activity. The test signal comprises a nerve stimulation signal for generating muscle activity, and/or the test signal comprises a muscle stimulation signal for generating muscle activity. It is already well known that specific nerve stimulation signals target specific nerve fibres. The nerve stimulation signal for activating muscles target so called Au nerve fibres. The muscle activity substantially only occurs when the nerve stimulation signal is directly applied near the Au nerve fibres and substantially have no effect when applied directly on muscle tissue (or muscle fibres) itself, unless the signal intensity is increased by, for example, an order of magnitude. Selecting such specific nerve stimulation signal as the electronic stimulation signal enables to use muscle contraction as an indicator that the location of the electrode is near to the nerve bundle comprising the A$\alpha$ nerve fibre. Pain suppression electrical signals generally are different electrical signals compared to the nerve stimulation signal for generating muscle activity because the pain suppression electrical signals target different nerve fibres in a nerve bundle, so called A$\beta$ nerve fibres. However, a nerve bundle generally comprises many types of nerve fibres including A$\alpha$-nerve fibres and A$\beta$-nerve fibres. By applying the nerve stimulation signal for generating muscle activity near the nerve bundle, the correct location with respect to the nerve bundle for muscle activity can be found. As the nerve bundle typically also comprises the A$\beta$ nerve fibres, the electrode location correct for muscle activity may also be used for applying the pain suppression electrical signal for pain suppression.

The muscle activity of, for example, a predefined muscle or the movement of a part of the body in response to the applying of the nerve stimulation signal for generating muscle activity may be used as an indicator that the electrode is in the vicinity of a specific nerve bundle which also comprises the A$\beta$ nerve fibre which may be targeted to apply the pain suppression signal for suppressing pain from a specific part of the human or animal body.

Finding the right location for applying the pain suppression signal is relatively difficult. One reason for this relatively difficult assessment of the right location is that the pain suppression due to the pain suppression signal does not immediately start when applying the pain suppression signal but typically only starts after the pain suppression signal is applied for some time. As such, a therapist generally has to interpret the indications of the patient to determine whether the chosen location which is electronically stimulated is the right location for pain suppression. However, when applying the test-signal being the nerve stimulation signal for generating muscle activity, the muscle which activates as a result of the signal may be used as a clear identifier which nerve or nerve bundle is targeted by the nerve stimulation signal for generating muscle activity, thus resulting in a clear and unambiguous feedback parameter to determine the location of the electrode, rather than often vague indications of a patient.

In an embodiment of the electrical stimulation device, the electrical stimulation device is configured for adapting a signal strength of the electrical stimulation signal applied to the electrodes of the matrix depending on the measured impedance of the individual electrode. A benefit of this embodiment is that it enables to compensation for local resistance differences.

In an embodiment of the electrical stimulation device, the electrical stimulation device is configured for applying a first electrical stimulation signal via a first electrode or via a first subset of electrodes, and for applying a second electrical stimulation signal different from the first electrical stimulation signal via a different electrode of the matrix of electrodes. The first electrical stimulation signal may, for example, be a FES signal and the second stimulation signal may, for example, be a TENS signal. This enables the electrical stimulation device to do both functional electrical stimulation and pain suppression either sequentially or simultaneously. Often, movement therapy is required for some patients recovering from a stroke. Such movement may be painful to the patient. In such a case, the therapy may include both pain suppression and functional electrical stimulation to improve the well-being of the patient while doing the movement therapy. Typically, both the location for applying the functional electrical stimulation signal and for applying the pain suppression signal are very close to each other or may even at the same location. In such an embodiment, the matrix of electrodes may be used to both apply the functional electrical stimulation signal and the pain suppression signal using the same electrode. As these stimulation signals are generally pulsed signals having predefined pulse wave duration, the pulses of the two different stimulation signals may be applied sequentially to achieve both the pain suppression and the functional stimulation. Alternatively, the two stimulation signals may be superposed and combined to a single signal provided to the electrode and having both the functional stimulation and pain suppression as a result. This combining of the two different stimulation signals into a single stimulation signal may be done using known signal superposition electronics which may be added to the electrical stimulation device.

According to a second aspect of the invention, the object is achieved with a method of locating an electrical stimulation point on a human or animal body via an electrical stimulation device, the electrical stimulation device comprising:
a matrix of electrodes distributed on an electrode pad being configured to be applied on the human or animal body,
the distribution of the electrodes in the matrix being arranged for covering a plurality of stimulation points of the human or animal,
an electronic circuit being connected to the electrodes of the matrix, and being configured for applying an electrical stimulation signal to the electrodes of the matrix, and
feedback means for providing a feedback signal to the electrical stimulation device in response to the applied electrical stimulation signal,
wherein the method comprises the step of:
applying the matrix of electrodes on the human or animal body, and wherein the method sequentially comprises the steps of:
applying the electrical stimulation signal to a subset of electrodes, and
receiving the feedback signal in response to the applying of the electrical stimulation signal.

The electrical stimulation signal may, for example, generate some recognizable active response which may be used to identify whether the location of the electrode is correct for applying a pain suppression signal. Such recognizable response may be caused by a visible muscle contraction caused by the applying of the electrical stimulation signal. Alternatively, this muscle contraction may substantially not be visible but may be measurable using a sensor or using the electrodes of the matrix as sensor. As such, the electrical stimulation points may be found via the method of locating the electrical stimulation points.

BRIEF DESCRIPTION OF THE DRAWINGS

These and other aspects of the invention are apparent from and will be elucidated with reference to the embodiments described hereinafter.

In the drawings.

The figures are purely diagrammatic and not drawn to scale. Particularly for clarity, some dimensions are exaggerated strongly. Similar components in the figures are denoted by the same reference numerals as much as possible.

DETAILED DESCRIPTION OF EMBODIMENTS

Figure 1:
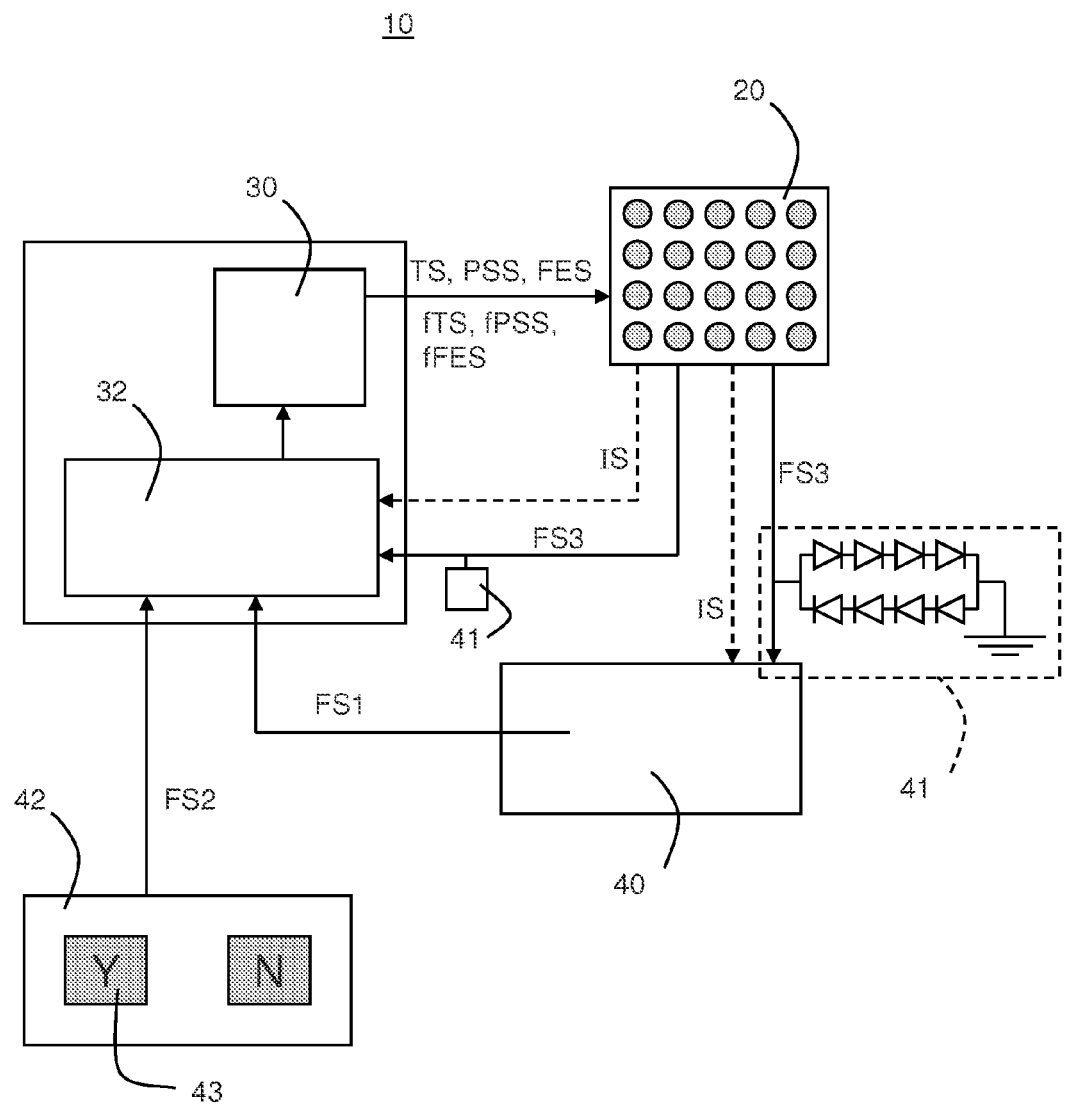
FIG. 1 shows a schematic view of an electrical stimulation device according to the invention.

FIG. 1 shows a schematic view of an electrical stimulation device 10 according to the invention. The electrical stimulation device 10 comprises an electrode pad 20 comprising a matrix of electrodes 120 ... 140 (see FIG. 3A) which may, for example, be applied on the skin of a human or animal for applying an electrical stimulation signal to the human or animal skin.

The electrical stimulation device 10 further comprises an electronic circuit 30 for generating an electrical stimulation signal TS, PSS, FES and feedback means 40, 42 for providing a feedback signal FS1, FS2, FS3 to the electrical stimulation device 10. The electrical stimulation device 10 as shown in FIG. 1 also comprises a controller 32 for controlling the electrical stimulation device 10. The controller 32 may, for example, instruct the electronic circuit 30 to generate a test-signal TS as electrical stimulation signal TS, PSS, FES for testing the current location of the electrode pad 20 on the human or animal skin. This test-signal TS comprises a nerve stimulation signal for generating muscle activity TS. This nerve stimulation signal for generating muscle activity TS is configured to only generate muscle activity when the electrode 120 . . . 140 through which the test signal TS is provided to the skin of the human or animal is in the neighbourhood of a motor-point 104 (see FIG. 2) or in the neighbourhood of a nerve bundle 100, 102 (see FIG. 2). When, in response of the test-signal TS, predetermined muscle activity is registered, the specific electrode 120 . . . 140 or the specific subset of electrodes 120 . . . 140 of the electrode pad 20 via which the test-signal is provided to the human or animal is near a specific nerve bundle 100, 102. As such, the currently selected electrode 120 . . . 140 or selected subset of electrodes 120 . . . 140 is at a possible right location on the skin of the human or animal to start other electrical stimulation signals TS, PSS, FES, such as pain suppression by providing the pain suppression signal PSS as the electrical stimulation signal TS, PSS, FES via the electrode 120 . . . 140.

The feedback signal FS1, FS2, FS3 may be a signal generated by the human or animal body in response to the applied electrical stimulation signal. Such feedback signal may be measurable at, for example, the skin of the human or animal. Due to the electrical stimulation signal TS, PSS, FES, for example, muscle tissue 106 may move or get activated which may be sensed at the skin of the human or animal body via known vibration measurements via a sensing means 40 or via known electrical measurements such as, for example, electromyogram signals via the sensing means 40. Alternatively, the electrical stimulation signal TS, PSS, FES may generate a visible muscle movement which may be clearly identified, even by a lay man. Due to the applying of the electrical stimulation signal TS, for example, a specific finger on the hand may move or twitch, or a specific muscle 106 may move or twitch which may be visible and which may be clearly identified. In such a situation, the feedback signal FS1, FS2, FS3 may be generated by an operator of the electrical stimulation device 10 to indicate whether the specific muscle-movement has been visually identified and as such is confirmed to the electrical stimulation device 10 by, for example, triggering a switch 43 generating the feedback signal FS2 via a key-pad 42.

The electrical stimulation device 10 is configured for sequentially applying the electrical stimulation signal TS, PSS, FES to subsets of electrodes 120 . . . 140 of the matrix, and for receiving the feedback signal FS1, FS2, FS3 in response to the applying of the electrical stimulation signal to the subsets of electrodes 120 . . . 140. The subset of electrodes 120 . . . 140 may be a single electrode 120 . . . 140 of the matrix, and as such the sequential applying of the electrical stimulation signal may result in sequentially applying the electrical stimulation signal to all electrodes of the matrix. Alternatively, the electrical stimulation signal TS, PSS, FES may be applied to more than one electrode 120 . . . 140 simultaneously, forming the subset of electrodes 120 . . . 140.

The electrical stimulation signal TS, PSS, FES causes a feedback signal FS1, FS2, FS3. By sequentially applying the electrical stimulation signal TS, PSS, FES to the subsets of electrodes 120 . . . 140 and by evaluating the feedback signal FS1, FS2, FS3, the suitability of the individual electrodes 120 . . . 140 of the matrix of electrodes 120 . . . 140 as electrical stimulation point is tested by the electrical stimulation device 10. The electrode pad 20 may be placed at a location where an optimum electrical stimulation point 132$s$, 138$s$ (see FIG. 3B) is expected to be located, for example, based on a rough estimate of a lay man's knowledge of the human or animal anatomy. Due to the sequential applying of the electrical stimulation signal TS, PSS, FES to subsets of electrodes 120 . . . 140, the electrodes 120 . . . 140 of the matrix located near to the electrical stimulation point 132$s$, 138$s$ will typically provide a predefined feedback which is recognised and which will enable the electrical stimulation device 10 to locate the best electrode 132, 138 or the best subset of electrodes 132, 138 as electrical stimulation electrode 132, 138.

Due to the use of the matrix of electrodes 120 . . . 140 and due to the sequential applying of the electrical stimulation signal TS, PSS, FES and the registration of the feedback FS1, FS2, FS3 in response to the applied electrical stimulation signal TS, PSS, FES to the subset of the electrodes 120 . . . 140, the exact location of the electrode pad 20 is less critical. The electrical stimulation device 10 tests the suitability of the individual electrodes 120 . . . 140 or the individual subsets of electrodes 120 . . . 140 using an electrical stimulation signal TS, PSS, FES to see which electrode 120 . . . 140 is near to the stimulation point 132$s$, 138$s$ and as such identifies the electrode 132, 138 or subset of electrodes 132, 138 suitable for use as stimulation electrode for applying the pain suppression signal PSS and/or the muscle stimulation signal FES. Subsequently, when the electrical stimulation device 10 has identified a suitable electrode 120 . . . 140 or subset of electrodes 120 . . . 140, the electrical stimulation device 10 may switch to a required stimulation signal PSS, FES to be applied via the selected electrode 132, 138 or subset of electrodes 132, 138. Alternatively, the user or therapist may activate the required stimulation signal PSS, FES upon an indication of the electrical stimulation device 10 that the electrical stimulation electrode 132, 138 has been found. As indicated before, the required stimulation signal PSS, FES may, for example, be a FES signal for muscle stimulation, or, for example, a pain suppression signal PSS, also indicated as TENS signal for pain suppression, or, for example, a TENS/FES combination signal to both provide muscle stimulation and pain suppression substantially simultaneously.

The sensing means 40 may, for example, comprise an electromyograph 40 for sensing an electromyogram signal, and/or an electroencephalograph 40 for sensing an electroencephalogram signal, and/or an magnetoencaphalograph 40 for sensing a magnetoencaphalogram signal in response of the electrical stimulation signal TS, PSS, FES. Alternatively, the sensing means 40 may be an acoustic sensor (not shown) or a piezo-electric sensor (not shown) for sensing muscle movement. The sensing means 40 may be connected to the electrode pad 20 such that the feedback signal FS1, FS2, FS3 is being sensed by the electrodes 120 . . . 140 of the matrix of electrodes 120, 140. In such a configuration, the electrodes 120 . . . 140 used for the sensing may be a further subset of electrodes 120 . . . 140 different from the electrodes 120 . . . 140 used for providing the electrical stimulation signal TS, PSS, FES. Because only a subset of the electrodes 120 . . . 140 is used for applying the electrical stimulation signal TS, PSS, FES, the remaining electrodes 120 . . . 140 of the electrode pad 20 may be available for sensing the feedback signal FS3. Alternatively, the electrodes 120 . . . 140 may be both used for applying the electrical stimulation signal TS, PSS, FES and for electrically sensing the feedback FS3 of the human or animal in response to the applied electrical stimulation signal TS, PSS, FES. Now, the electrical stimulation device 10 may be able to sense at the exact same location as the electrical stimulation signal TS, PSS, FES is applied. In an alternative embodiment the sensing means 40 may be integrated in the controller 32 and the feedback signal FS3 may be directly interpreted by the controller 32.

The electrodes used for sensing the feedback signal FS3 may be clipped via clipping-circuit 41. The clipping-circuit 41 may, for example disable measurement during predefined time-window (not shown) after applying stimulation signal or via a diode-based clipping-circuit 41 (illustrated in FIG. 1). Experimentally, the inventors have found that due to the used sensing electronics, a time-window of 2 milliseconds directly after the stimulation pulse of the electrical stimulation signal TS, PSS, FES may be sufficient to clip the sensor 40 to ensure good electrical measurement of the feedback signal. A shorter time-window may be possible, depending on the sensing electronics. In the diode-based clipping circuit 41, a set of diodes arranged antiparallel may be connected at one end to the connector between the electrode and the sensing means 40 and at the opposite end to ground. The break-down voltage of the diodes must be chosen such that no signal above the clipping voltage can reach the sensing electronics of the sensing means 40.

The controller 32 or the sensing means 40 may, for example, next to receiving the feedback signal FS3 from the electrode pad 20, also receive an impedance signal IS from the electrode pad 20. Such an impedance signal IS represents the impedance of the skin of the human or animal at the locations of the electrodes 120 . . . 140 of the electrode pad 20. This impedance measurement may be used, for example, before applying the test-signal TS to ensure that the electrode pad 20 is correctly applied to the skin of the human or animal. Furthermore, the impedance measurement may be used to provide an indication whether the electrode pad 20 is located in the vicinity of a nerve 104 or nerve bundle 100, 102 and that the applying of the nerve stimulation signal for generating muscle activity TS may generate any muscle activity at all. As the impedance of the skin of the human or animal in the vicinity of the nerve 104 or the nerve bundle 100, 102 is typically substantially lower compared to the impedance of the skin of the human or animal away from the nerve, the impedance measurement provides an indication whether a nerve 104 or nerve bundle 100, 102 is nearby. If the impedance measured at the electrode location is not below a certain threshold, applying of the test-signal TS, PSS, FES would probably not result in any feedback FS1, FS2, FS3 at all. Still, care should be taken as the impedance measurement typically only identifies electrical stimulation points which are located near the surface of the skin. Also other stimulation point may be required and should be found and thus only relying on impedance measurement for finding the stimulation points is typically not sufficient.

The measurement of the impedance of the individual electrodes 120 . . . 140 in the electrode pad 20 may be used to make a preselection of electrodes 120 . . . 140 from the electrode pad 20 which may be used for providing the test-signal TS according to the current invention to test the location of the electrical stimulation points.

The received impedance signal IS from the electrode pad 20 may also be used to adapt the parameters of the electrical stimulation signal TS, PSS, FES to the further electrical stimulation signal fTS, fPSS, fFES for generating muscle activity. If, for example, the impedance value measured at the current electrode pad 20 location is relatively high, the intensity of the electrical stimulation signal TS, PSS, FES for generating muscle activity may have to be adapted to ensure that the expected muscle activity is registered. Alternatively, a second sequential selection of a subset of electrodes 120 . . . 140 may be tested using an electrical stimulation signal fTS, fPSS, fFES having reduced intensity to find the stimulation point requiring lowest signal power to provide electrical stimulation.

In an embodiment of the electrical stimulation device 10, the stimulation device 10 may, for example, be configured for applying a first stimulation signal FES comprising a functional stimulation signal FES for functionally stimulating muscle activity via a first electrode 120 . . . 140 or a first subset of electrodes 120 . . . 140 and for applying a second stimulation signal PSS comprising a pain suppression signal PSS via a second electrode 120 . . . 140 or a second subset of electrodes 120 . . . 140 from the electrode pad 20. Often, movement therapy is required for some patients recovering from a stroke. Such movement may be painful to the patient. In such a case, the therapy may include both pain suppression and functional electrical stimulation to improve the well-being of the patient while doing the movement therapy. Typically, the location for applying the functional electrical stimulation signal FES and for applying the pain suppression signal PSS are close to each other or even overlap. In such an embodiment, an electrode pad 20 may be used to apply both the functional electrical stimulation signal FES and the pain suppression signal PSS using different electrodes 120 . . . 140 from the matrix of electrodes 120 . . . 140. As these stimulation signals PSS, FES are generally pulsed signals having predefined pulse wave duration, the pulses of the two different stimulation signals may be applied, for example, sequentially to achieve both the pain suppression and the functional stimulation. Alternatively, the two stimulation signals PSS, FES may be applied simultaneously to different electrodes 120 . . . 140 of the matrix of electrodes 120 . . . 140. In such an embodiment, the electrical stimulation device 10 may have an electronic circuit 30 which may generate both the functional electrical stimulation signal FES and the pain suppression signal PSS simultaneously or consecutively. The electrical stimulation device 10 may comprise two different electronic circuits (not shown), one for the generation of the functional stimulation signal FES and one for generating the pain suppression signal PSS.

The electrical stimulation device 10 may be configured for applying the functional stimulation signal FES and the pain suppression signal PSS sequentially or simultaneously to the same electrode 120 . . . 140 or to the same subset of electrodes 120 . . . 140. In such an embodiment, the stimulation signal TS, PSS, FES comprises both the functional stimulation signal FES for functionally stimulating muscle activity and the pain suppression signal PSS. A benefit of this embodiment is that typically the same nerve bundle 100, 102 is targeted when applying the functional electrical stimulation signal FES for the movement therapy and when applying the pain suppression signal PSS for suppressing the pain when moving. When the surface of the individual electrodes 120 . . . 140 is relatively large, the optimum location of applying the functional stimulation signal FES and the pain suppression signal PSS overlap and have to be supplied via the same electrode 120 . . . 140 or the same subset of electrodes 120 . . . 140. As indicated above, the stimulation signals TS, PSS, FES are generally pulsed signals having predefined pulse wave duration for targeting different nerve fibers. As such, the two stimulation signals may be superposed and combined to a single signal provided to the same electrode 120 . . . 140 or the same subset of electrodes 120 . . . 140 and having both the functional stimulation and pain suppression as a result. Alternatively, the two stimulation signal pulses may be applied sequentially to the human or animal via the same electrode 120 . . . 140 or same subset of electrodes 120 . . . 140. Again, known signal superposition electronics may be used.

Figure 2:
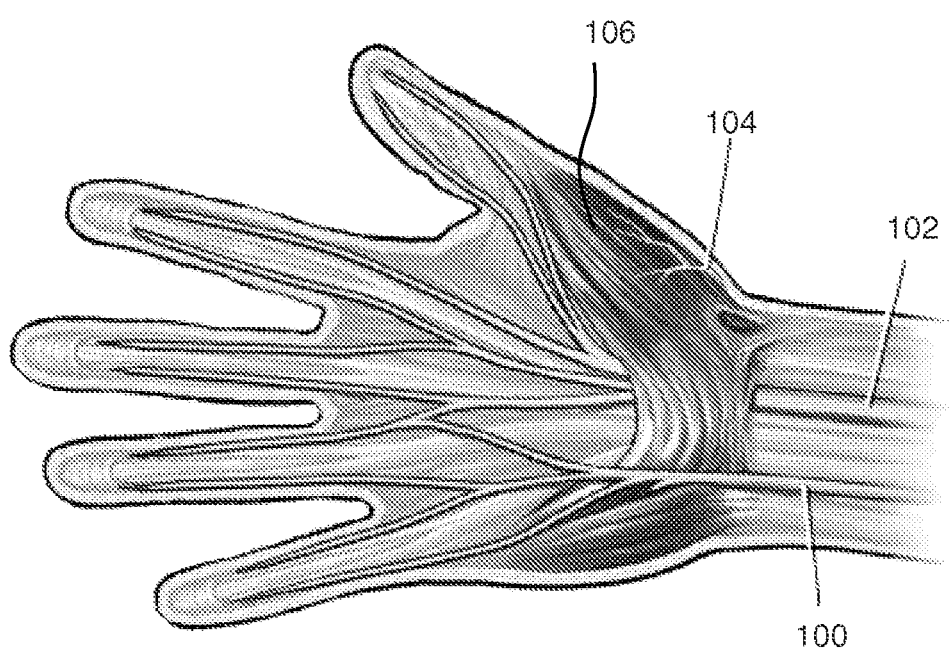
FIG. 2 shows a layout of muscles, nerves and nerve bundles in a hand.

FIG. 2 shows a layout of muscles 106, nerves 104 and nerve bundles 100, 102 in a hand. As can be clearly seen from FIG. 2, the nerves controlling the movement and touch of the individual fingers of the hand group together in a specific nerve bundles 100, 102. As such, to suppress the pain in a certain part of the hand, for example, in the thumb, a certain nerve bundle 102 of the available nerve bundles 100, 102 should be targeted with the pain suppression signal PSS. When providing the nerve stimulation signal for generating muscle activity TS to the nerve bundle indicated with reference number 102, the thumb moves or twitches, indicating that the selected electrode 120 . . . 140 of the electrode pad 20 is located near enough to the nerve bundle indicated with reference number 102 to stimulate the Aα nerve fibers in this nerve bundle 102. Nerve 104 indicates a motor-point 104 and represents a different electrical stimulation point. For applying very selective movement therapy of the thumb of this specific person, the motor-point 104 may require a functional stimulation signal FES. When applying the test-signal TS via an electrode 120 . . . 140 near the motor-point 104, only this muscle of the thumb will move, while when applying the test-signal TS to the stimulation point near the nerve bundle indicated with reference number 102, more than just the thumb moves or twitches. As such, the exact location of both the motor-point 104 and the nerve bundle 102 may be identified. The pain suppression signal PSS may, for example, be applied via the nerve bundle 102 and at the same time, muscle stimulation may be performed via applying a functional stimulation signal FES via the motor-point 104. As such, both pain suppression and functional stimulation may be performed on the required location via identifying the stimulation points of the human or animal after sequentially testing the different electrodes 120 . . . 140 of the electrode pad 20 comprising the matrix of electrodes 120 . . . 140.

Figure 3A:
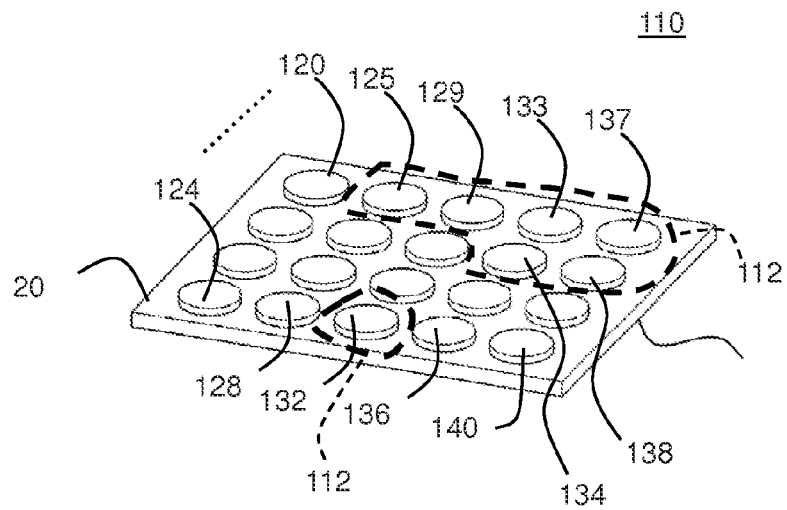
FIG. 3A shows a layout of a electrode-matrix for use with the electrical stimulation device according to the invention.
Figure 3B:
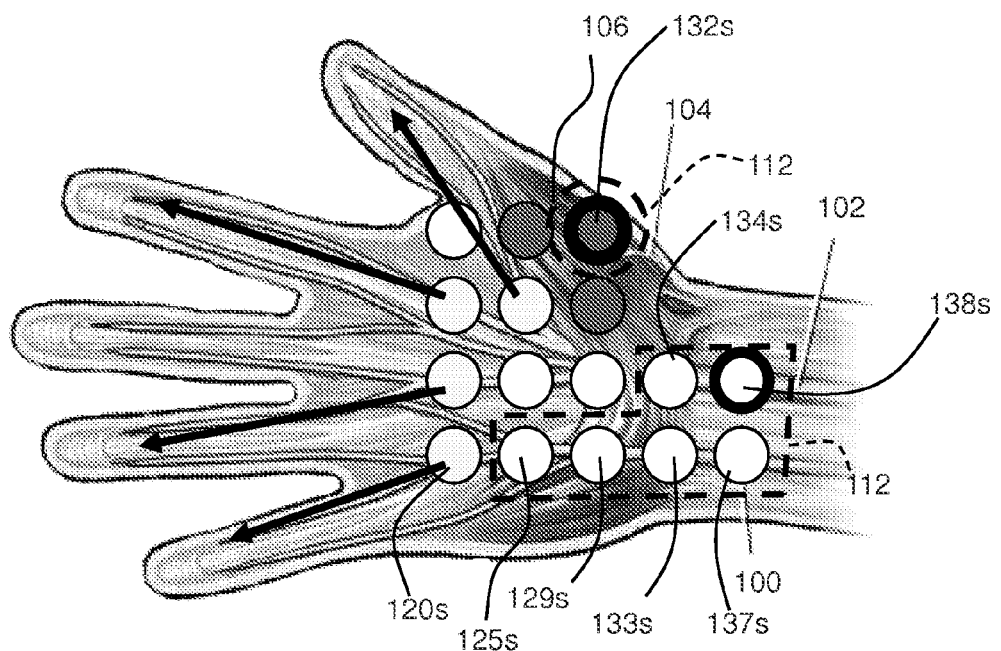
FIG. 3B shows a possible applying of the electrode-matrix to a hand and indicates possible electrical stimulation points in the hand.

FIG. 3A shows a layout of an electrode-matrix 110 for use with the electrical stimulation device 10 according to the invention. FIG. 3B shows a possible applying of the electrode-matrix 110 to a hand and indicates possible contact point of the individual electrodes 120 . . . 140 on the hand and possible electrical stimulation points in the hand. The stimulation points which correspond to the electrodes 120 . . . 140 of the electrode-matrix 110 are indicated with a similar reference number further comprising the letter 's'. The electrodes 120 . . . 140 of the electrode-matrix 110 are numbered sequentially row by row. In the electrode-matrix 110 indicated in FIG. 3A a sub-set 112 of electrodes 125, 129, 132, 133, 134, 137, 138 is indicated. This sub-set 112 may, for example, result from initial impedance measurements of the electrodes 120 . . . 140 of the electrode-matrix 110 and only selecting the electrodes 120 . . . 140 from the electrode-matrix 110 which have an impedance value below a certain threshold value or which have an impedance value different from an average impedance value of all the electrodes 120 . . . 140 of the electrode-matrix 110. The electrodes 125, 129, 132, 133, 134, 137, 138 of the sub-set 112 are located relatively near to a nerve 104 or nerve bundle 100, 102 and as such may be used for supplying the test-signal TS and/or for supplying functional stimulation signal FES and/or for supplying the pain suppression signal PSS. When applying the test-signal TS being the nerve stimulation signal for stimulating muscle activity TS sequentially to the individual electrodes 125, 129, 132, 133, 134, 137, 138 of the sub-set 112, the active response of the hand of the human in response to the test-signal TS will be different for each of the electrodes 125, 129, 132, 133, 134, 137, 138 in the sub-set 112. For example, when the test-signal TS is applied to the electrode having reference number 138, the stimulation point having reference number 138s will be stimulated which results in stimulation of the nerve bundle 102 and a different set of fingers of the hand that will move in response to the test-signal TS compared to when applying the test-signal TS to the electrode having reference number 137 which will stimulate the stimulation point having reference number 137s. In both cases a nerve bundle 102, 100 is stimulated by the respective electrodes 138, 137. However the Aα nerve fibers differ in the respective nerve bundles 102, 100 which results in a different active response from the test-signal TS. If Aδ nerves of the first nerve bundle having reference number 102 must be stimulated for pain suppression, the stimulation point having reference number 138s must be selected and the predefined active response from stimulating the first nerve bundle 102 using the test-signal TS must be used to correctly identify the electrode 138 capable of stimulating the first nerve bundle 102.

Alternatively, the test-signal TS may be applied via electrode having reference number 132 which will stimulate the stimulation point having reference number 132s. The applying of the test-signal TS via the electrode with reference number 132 will stimulate the motor-point 104 which will clearly be identifiable because substantially only the thumb of the human will move and/or twitch. This location may, for example, be used for the functional stimulation signal FES to stimulate the specific movement of the thumb via the motor-point 104.

Furthermore, from the example shown in FIGS. 3A and 3B it is clear that the subset 112 of electrodes 125, 129, 132, 133, 134, 137, 138 does not necessarily have to be a group of adjacent electrodes. The subset 112 of electrodes 125, 129, 132, 133, 134, 137, 138 may be any subset 112 which complies to the requirements, in this case having an impedance value below a certain threshold. In the current embodiment, the impedance measurement of all the electrodes 120 . . . 140 of the electrode-matrix 110 enables to find the sub-set 112 of electrodes 125, 129, 132, 133, 134, 137, 138. Next the test-signal TS will be applied to each electrode 125, 129, 132, 133, 134, 137, 138 of the sub-set 112 and the active response is registered to find the specific electrode 138 which may be used to provide the pain suppression signal PSS to the first nerve bundle 102. Alternatively, the test-signal TS may be sequentially applied to each of the electrodes 120 . . . 140 of the electrode-matrix 110 without first doing the impedance measurement. This selection of the correct electrode 138 without applying the impedance measurement possibly takes some more time, but it enables the electrical stimulation device 10 to be less complex as no means for impedance measurement have to be present. Furthermore, it enables the electrical stimulation device to also identify stimulation points which may be located deeper into the skin of the human or animal. Such stimulation points located deeper into the skin may not be found when applying impedance measurements.

The predetermined response when stimulating the first nerve bundle 102 via the test-signal TS may, for example, be achieved when providing the test-signal TS via two electrodes indicated with the reference numbers 134 and 138. A second applying of the test-signal TS, for example, using a test-signal TS having reduced intensity, to the two electrodes having reference number 134 and 138 may reveal that the signal required for obtaining the predetermined response is larger for the electrode indicated with reference number 134 compared to the electrode indicated with reference number 138. The applying of the test-signal TS having reduced intensity may result in a visible (or measureable) feedback only when the test-signal TS is applied via the electrode having reference number 138. As such, the optimum electrode 138 for providing the pain suppression signal PSS to the hand is via the electrode indicated with reference number 138. Subsequently the electrical stimulation device 10 according to the invention starts to suppress pain in the hand by providing the pain suppression signal PSS via the electrode indicated with reference number 138. Simultaneously or sequentially, a functional stimulation signal FES for functionally stimulating muscle activity may be applied via the same electrode 138 for simultaneously provide functionally stimulation of the muscles and suppress pain. Alternatively, a further electrode having reference number 132 may be used for providing a function stimulation signal FES to the motor-point indicated with reference number 104 to directly stimulate the muscle 106 in the hand.

The electrical stimulation device 10 may be configured for sensing the feedback signal FS1, FS2, FS3 using a plurality of electrodes 120 . . . 140 from the matrix 110 distributed across the matrix 110. This feedback signal FS1, FS2, FS3 distributed across the matrix 110 may be used for sensing a so called feedback-map (not shown) showing a distribution of possible measurement points across an area resulting from the electrical stimulation signal TS, PSS, FES. Such feedback-map may be used to, for example, to identify a specific location on the human or animal body where the matrix 110 of electrodes is currently applied. Using such feedback-map may enable the electrical stimulation device 10 to find already identified electrical stimulation points 138, 132 relatively easily by comparing the sensed feedback-map with a stored feedback-map. This stored feedback may be, for example, a feedback-map of earlier measurements of the electrical stimulation device 10 or may be generated by the producer of the electrical stimulation device 10 and may represent specific locations on the human or animal body which are relatively common for applying electrical stimulation signals. The comparison with a stored feedback enables to identify what body-part the matrix 110 is currently applied to and how far the matrix 110 is shifted and/or rotated in a certain direction with respect to the stored feedback-map. If the stored feedback also comprises the preferred stimulation location, the electrical stimulation device may, from the information of the shift and/or rotation of the matrix 110 with respect to the stored feedback-map, directly derive which electrode 120 . . . 140 or subset of electrodes 120 . . . 140 to use for providing the electrical stimulation signal TS, PSS, FES. Furthermore, the stored feedback may comprise different stimulation points, for example, a preferred FES stimulation point and a preferred TENS stimulation point to suppress pain when stimulating the muscle via the FES point. In such a way, a misalignment of the matrix 110 of electrodes 120 . . . 140 is quickly identified and may quickly be electrically compensated for by choosing an electrode 120 . . . 140 or subset of electrodes 120 . . . 140 based on the sensed misalignment information. A similar or alternative feedback-map may also be based on impedance measurements and may be compared, for example, by a stored feedback also based on impedance measurements. As impedance measurements may be done relatively quickly and substantially without pain for the human and/or animal, this initial feedback map based on impedance measurements may also be used for identifying the location of the matrix 110 on the skin and to determine a shift and/or rotation of the matrix 110 on the skin.

Figure 4A:
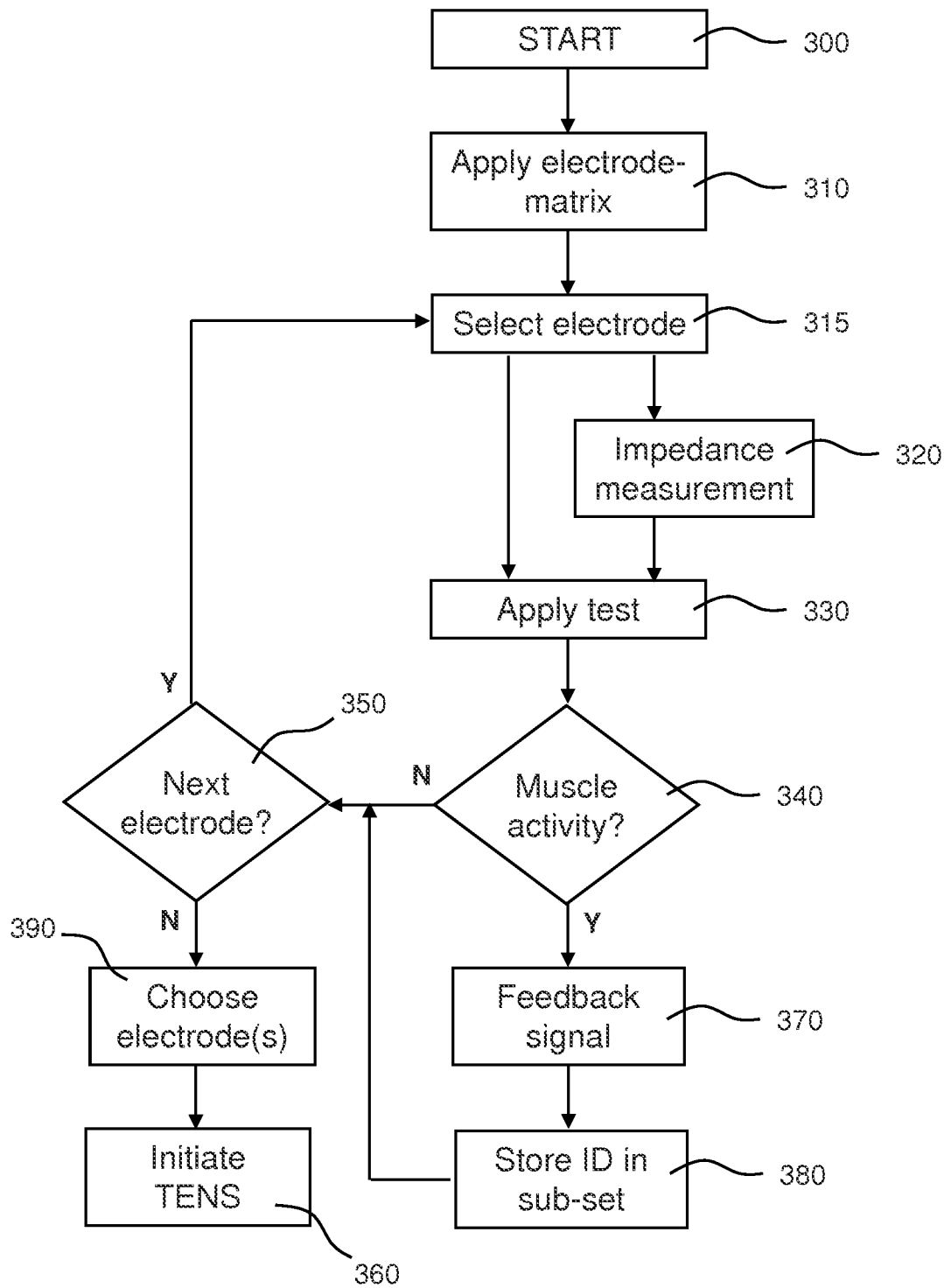
FIGS. 4A and 4B show a flow-diagram of locating a nerve for electrical stimulation in an embodiment of the electrical stimulation device having an electrode-matrix, in which FIG. 4B provides detailed steps of selecting electrodes from the electrode-matrix.
Figure 4B:
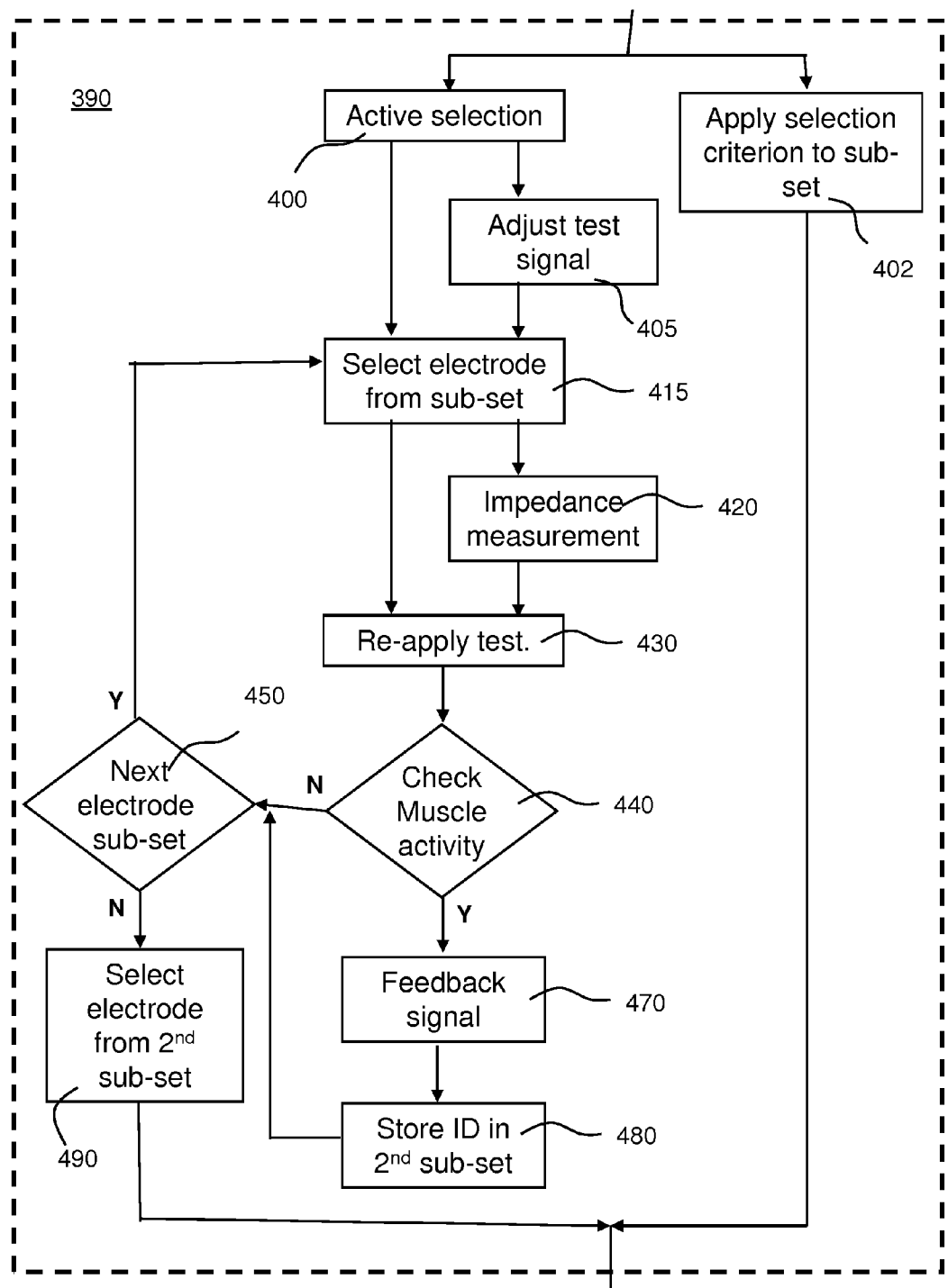

FIGS. 4A and 4B show a flow-diagram of locating a nerve for electrical stimulation in an electrode-matrix 110 according to the invention. FIG. 4B provides detailed steps of selecting electrodes 120 . . . 140 from the electrode-matrix 110. In FIG. 4A the flow-diagram starts with the step START 300 after which the step APPLY ELECTRODE-MATRIX 310 is performed for applying the electrode-matrix 110 on the human or animal body. Next the step SELECT ELECTRODE 315 is performed for selecting an electrode 120 . . . 140 from the electrode-matrix 110. Optionally, an intermediate step of IMPEDANCE MEASUREMENT 320 may be performed for measuring the impedance of the selected electrode selected in the step SELECT ELECTRODE 315. Depending on the impedance measurement, the test-signal may not be applied to the selected electrode (this option is not shown in the flow-diagram of FIG. 4A). Next, the test-signal TS is applied to the selected electrode in the step of APPLY TEST 330. Subsequently, the active response is monitored in the step MUSCLE ACTIVITY 340. If no muscle activity is registered, the flow-diagram tests if there are still electrodes not tested in the electrode-matrix 110 in the step NEXT ELECTRODE? 350. If there are still un-tested electrodes in the electrode-matrix 110, the step SELECT ELECTRODE 315 will select the next un-tested electrode from the electrode-matrix 110 after which the applying of the test-signal TS is done. If the is muscle activity in the step of monitoring MUSCLE ACTIVITY 340, a feedback signal may be provided to the electrical stimulation device 10 in the step FEEDBACK SIGNAL 370 and subsequently an identification of the selected electrode 120 . . . 140 is stored in a memory of the electrical stimulation device 10 in the sub-set 112. Next, the flow-diagram tests if there are still electrodes not tested in the electrode-matrix 110 in the step NEXT ELECTRODE? 350. If there are no more un-tested electrodes 120 . . . 140 in the electrode-matrix 110, the flow-diagram will select an electrode from the sub-set 112 in the step CHOOSE ELECTRODE 390 and subsequently pain suppression may commence in the step INITIATE TENS 360.

Instead of individual electrodes 120 . . . 140 which are selected in the step SELECT ELECTRODE 315, also a subset of electrodes 120 . . . 140 may simultaneously be selected in the step SELECT ELECTRODE 315. This may be beneficial when the dimensions of the electrodes are reduced to, for example, sub millimeter dimensions. The electrode pad 20 may then comprise thousands of electrodes 120 . . . 140 which would result in a relatively time-consuming testing of all the electrodes 120 . . . 140 individually. In such a case, the initially subsets of electrodes 120 . . . 140 may be selected to roughly identify the location of possible stimulation points after which a more accurate determination of the electrode or further subset of electrodes may be done to accurately identify the required stimulation point.

The step of IMPEDANCE MEASUREMENT 320 may be applied to all electrodes 120 . . . 140 of the electrode-matrix 110 before the test-signal TS is applied to any of the electrodes 120 . . . 140 of the electrode-matrix 110 or the any of the subsets of electrodes 120 . . . 140. The impedance measurement is done as a pre-selection criterion in that, for example, only electrodes 120 . . . 140 from the electrode-matrix having an impedance value below a certain threshold or below the average impedance value of all electrodes 120 . . . 140 of the electrode-matrix 110 form the sub-set 112 of electrodes, After the sub-set 112 has been selected via the impedance measurement, the test-signal TS may be applied to the individual electrodes of the sub-set 112 for selecting the electrode from the sub-set 112 which may be used to provide the pain suppression signal PSS or the functional stimulation signal FES.

FIG. 4B shows a flow-diagram indicated in more detail how the electrode used for providing the pain suppression signal PSS may be selected. The more detailed selection procedure may, for example, comprise any selection criterion for selecting an electrode from the sub-set 112, which is illustrated in the flow-diagram of FIG. 4B by the optional step APPLY SELECTION CRITERION TO SUB-SET 402. Alternatively, the active selection procedure will start with the step ACTIVE SELECTION 400. Optionally, the test-signal TS is adjusted, for example, the signal strength or amplitude of the test-signal TS is reduced in the optional step ADJUST TEST SIGNAL 405. Next, an electrode from the sub-set 112 is selected in the step SELECT ELECTRODE FROM SUB-SET 415. Optionally an impedance measurement may again be performed in the step IMPEDANCE MEASUREMENT 420. Next the adjusted test-signal TS may be re-applied to the selected electrode from the sub-set 112 in the step RE-APPLY TEST 430. Again, the active response is monitored in the step MUSCLE ACTIVITY 440 and if no muscle activity is monitored, the procedure checks whether there are still electrodes in the sub-set 112 which have not been selected in the step NEXT ELECTRODE SUB-SET 450. If muscle activity is monitored using the adjusted test-signal TS, a feedback signal is provided to the electrical stimulation device 10 in the step FEEDBACK SIGNAL 470 and an identification of the selected electrode is stored in a memory of the electrical stimulation device 10 in the step STORE ID IN $2^{ND}$ SUB-SET 480. Subsequently return to the step of NEXT ELECTRODE SUB-SET 450 to select a next electrode from the sub-set 112 to apply the adjusted test-signal TS. If all electrodes from the sub-set 112 have been tested using the adjusted test-signal TS, a selection is made from the stored electrodes from the second sub-set in the step SELECT ELECTRODE FROM $2^{ND}$ SUB-SET 490. If more than one electrode is stored in the second sub-set, a further selection criteria may be used to choose from that second sub-set of electrodes or the active selection may be re-applied using a further adjusted test-signal TS.

Alternatively, the selection criteria for selecting the electrode via which the pain suppression signal PSS or the functional stimulation signal FES will be applied to the human or animal may include selecting all or a plurality of electrodes of the sub-set 112 or of the second sub-set. In such an embodiment the pain suppression signal PSS or the functional stimulation signal FES will be provided via a plurality of electrodes parallel which enables the signal intensity for each individual electrode of the pain suppression signal PSS and/or the functional stimulation signal FES to be reduced thus making the pain suppression or muscle stimulation more comfortable for the human or animal.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements or by means of software. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An electrical stimulation device for locating an electrical stimulation point on a human or animal body, the electrical stimulation device comprising:

a matrix of electrodes distributed on an electrode pad configured to be applied on the human or animal body, the matrix of electrodes arranged for covering a plurality of the stimulation points of the human or animal;

an electronic circuit connected to the matrix of electrodes and configured to apply an electrical stimulation signal to the electrodes, the electronic circuit configured to sequentially apply the electrical stimulation signal to subsets of electrodes of the matrix; and feedback means configured to provide a feedback signal in response to an application of the electrical stimulation signal.

2. The device of claim 1, wherein the feedback signal comprises visible muscle movement of the human or animal in response to the application of the electrical stimulation signal to one or more electrodes of the matrix.

3. The device of claim 1, wherein the feedback means comprises:

sensing means for sensing the feedback signal of the human or animal in response to the application of the electrical stimulation signal to one or more electrodes; and a switch for generating the feedback signal in response to activation of the switch.

4. The device of claim 3, wherein a subset of electrodes is configured to sense the feedback signal of the human or animal in response to the application of the electrical stimulation signal.

5. The device of claim 3, wherein the electrodes are configured to apply the electrical stimulation signal and to sense the feedback signal of the human or animal.

6. The device of claim 3 further comprising;

diode-based clipping circuitry, the diode-based clipping circuitry configured to disable measurement of the feedback signal during a predefined time-window after application of the electrical stimulation signal to dip the feedback signal.

7. The device of claim 4, wherein the electrical stimulation signal is subsequently applied to one or more subsets of electrodes for subsequently sensing the feedback signal from a plurality of electrodes distributed across the matrix.

8. The device of claim 7, wherein the sensed feedback signal is compared with a stored feedback signal.

9. The device of claim 5, wherein the electrical stimulation signal is applied to an electrode of the matrix, and the feedback signal from the electrode is compared to one or more feedback signals measured at electrodes located around the electrode receiving the electrical stimulation signal for identifying a motor point as electrical stimulation point.

10. The device of claim 1, wherein the electronic circuit is configured to sequentially apply a further electrical stimulation signal to the subsets of electrodes of the matrix, the further electrical stimulation signal having a different intensity as compared to the electrical stimulation signal.

11. The device of claim 1, wherein the electronic circuit is configured to measure an impedance of the electrodes before application of the electrical stimulation signal, or before application of the further electrical stimulation signal, or before application of the electrical stimulation signal and before application of the further electrical stimulation signal.

12. The device of claim 1, wherein the electrical stimulation signal comprises one or more of: a test signal, a pain suppression signal, and an electrical stimulation signal for generating muscle activity.

13. The device of claim 12, wherein the test signal comprises one or more of a nerve stimulation signal for generating muscle activity, and a muscle stimulation signal for generating muscle activity.

14. The device of claim 11, wherein the electronic circuit is configured to adapt a signal strength of the electrical stimulation signal applied to the electrodes of the matrix depending on the measured impedance of the electrode.

15. A method of locating an electrical stimulation point on a human or animal body comprising:
    applying a matrix of electrodes to a one of human and an animal body, the matrix of electrodes distributed on an electrode pad;
    applying an electrical stimulation signal to one or more electrodes of a subset of electrodes of the matrix of electrodes;
    sensing a feedback signal from one or more electrodes of the subset of electrodes in response to an application of the electrical stimulation signal; and
    comparing the feedback signal to one or more feedback signals measured at electrodes located around the one or more electrodes receiving the electrical stimulation signal for identifying an electrical stimulation point.

16. The method of claim 15, wherein the matrix of electrodes is arranged on the electrode pad for covering a plurality of the stimulation points of a human or animal.

17. The method of claim 15, wherein the feedback signal is compared to one or more feedback signals measured at electrodes located around the electrode receiving the electrical stimulation signal for identifying a motor point as the electrical stimulation point.

18. The method of claim 15 further comprising:
    sequentially applying a further electrical stimulation signal to subsets of electrodes of the matrix, the further electrical stimulation signal having a different intensity as compared to the electrical stimulation signal.

19. The method of claim 15 further comprising:
    performing one or more of: measuring an impedance of the electrodes before applying the electrical stimulation signal, or before applying the further electrical stimulation signal, or before applying the electrical stimulation signal and before applying the further electrical stimulation signal.

20. The method of claim 15, wherein the electrical stimulation comprises one or more of: a test-signal, a pain suppression signal, and an electrical stimulation signal for generating muscle activity.

* * * * *